United States Patent
Jacobsen et al.

(10) Patent No.: US 11,478,304 B2
(45) Date of Patent: Oct. 25, 2022

(54) FLEXIBLE CIRCUIT COILS

(71) Applicant: Medtronic Navigation, Inc., Louisville, CO (US)

(72) Inventors: Brad Jacobsen, Erie, CO (US); Bruce M. Burg, Louisville, CO (US); Andrew Bzostek, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 692 days.

(21) Appl. No.: 14/674,766

(22) Filed: Mar. 31, 2015

(65) Prior Publication Data

US 2016/0287342 A1    Oct. 6, 2016

(51) Int. Cl.
| | |
|---|---|
| A61B 34/20 | (2016.01) |
| A61B 5/06 | (2006.01) |
| A61B 5/00 | (2006.01) |
| A61B 17/00 | (2006.01) |
| A61N 2/00 | (2006.01) |
| A61M 25/01 | (2006.01) |

(52) U.S. Cl.
CPC .............. *A61B 34/20* (2016.02); *A61B 5/062* (2013.01); *A61B 5/6853* (2013.01); *A61B 2017/00725* (2013.01); *A61B 2017/00862* (2013.01); *A61B 2034/2046* (2016.02); *A61B 2034/2051* (2016.02); *A61B 2034/2068* (2016.02); *A61M 2025/0166* (2013.01); *A61M 2205/3317* (2013.01); *A61N 2/006* (2013.01)

(58) Field of Classification Search
CPC ....... A61B 34/20; A61B 5/062; A61B 5/6853; A61B 2034/2051; A61M 25/10; A61F 2/013; A61F 2/958
See application file for complete search history.

(56) References Cited

U.S. PATENT DOCUMENTS

| | | | | |
|---|---|---|---|---|
| 5,171,299 A | * | 12/1992 | Heitzmann | A61M 25/104 604/100.03 |
| 5,348,010 A | | 9/1994 | Schnall et al. | |
| 5,752,522 A | * | 5/1998 | Murphy | A61B 5/1076 600/505 |
| 8,046,052 B2 | | 10/2011 | Verard et al. | |
| 8,644,907 B2 | | 2/2014 | Hartmann et al. | |
| 2007/0244394 A1 | * | 10/2007 | Greenan | A61B 5/06 600/470 |

(Continued)

FOREIGN PATENT DOCUMENTS

| | | |
|---|---|---|
| EP | 2151209 A2 | 2/2010 |
| EP | 2505227 A1 | 10/2012 |
| EP | 1585434 B1 * | 1/2015 ............. A61B 34/20 |

OTHER PUBLICATIONS

International Preliminary Report on Patentability dated Oct. 12, 2017 in corresponding International Application No. PCT/US2016/023869.

(Continued)

*Primary Examiner* — Oommen Jacob
*Assistant Examiner* — Nyrobi Celestine
(74) *Attorney, Agent, or Firm* — Harness, Dickey & Pierce, P.L.C.

(57) ABSTRACT

Disclosed is a system for determining a location and configuration of an expandable member. A flexible coil can be provided on a shape changing portion, such as an expandable portion, to measure a signal as the shape changes.

16 Claims, 4 Drawing Sheets

(56) References Cited

U.S. PATENT DOCUMENTS

| | | | | |
|---|---|---|---|---|
| 2008/0269868 A1* | 10/2008 | Bei | ................ | A61F 2/013 |
| | | | | 623/1.11 |
| 2010/0030063 A1 | 2/2010 | Lee et al. | | |
| 2012/0253167 A1* | 10/2012 | Bonyak | ................ | A61B 5/6885 |
| | | | | 600/409 |
| 2014/0148692 A1 | 5/2014 | Hartmann et al. | | |
| 2014/0323852 A1 | 10/2014 | Wald et al. | | |
| 2015/0238275 A1* | 8/2015 | Kung | ................ | A61B 5/1073 |
| | | | | 600/424 |
| 2015/0374483 A1* | 12/2015 | Janardhan | ................ | A61F 2/013 |
| | | | | 606/200 |
| 2016/0183807 A1* | 6/2016 | Schoenle | ................ | A61B 5/0066 |
| | | | | 600/437 |

OTHER PUBLICATIONS

Extended European Search Report regarding International Application No. 20213535.6, dated Sep. 9, 2021.
European Office Action regarding European Patent Application No. 16717499.4, dated Nov. 19, 2019.
International Search Report and Written Opinion dated Jun. 24, 2016 for PCT/US2016/023869 claiming benefit of U.S. Appl. No. 14/674,766, filed Mar. 31, 2015.

\* cited by examiner

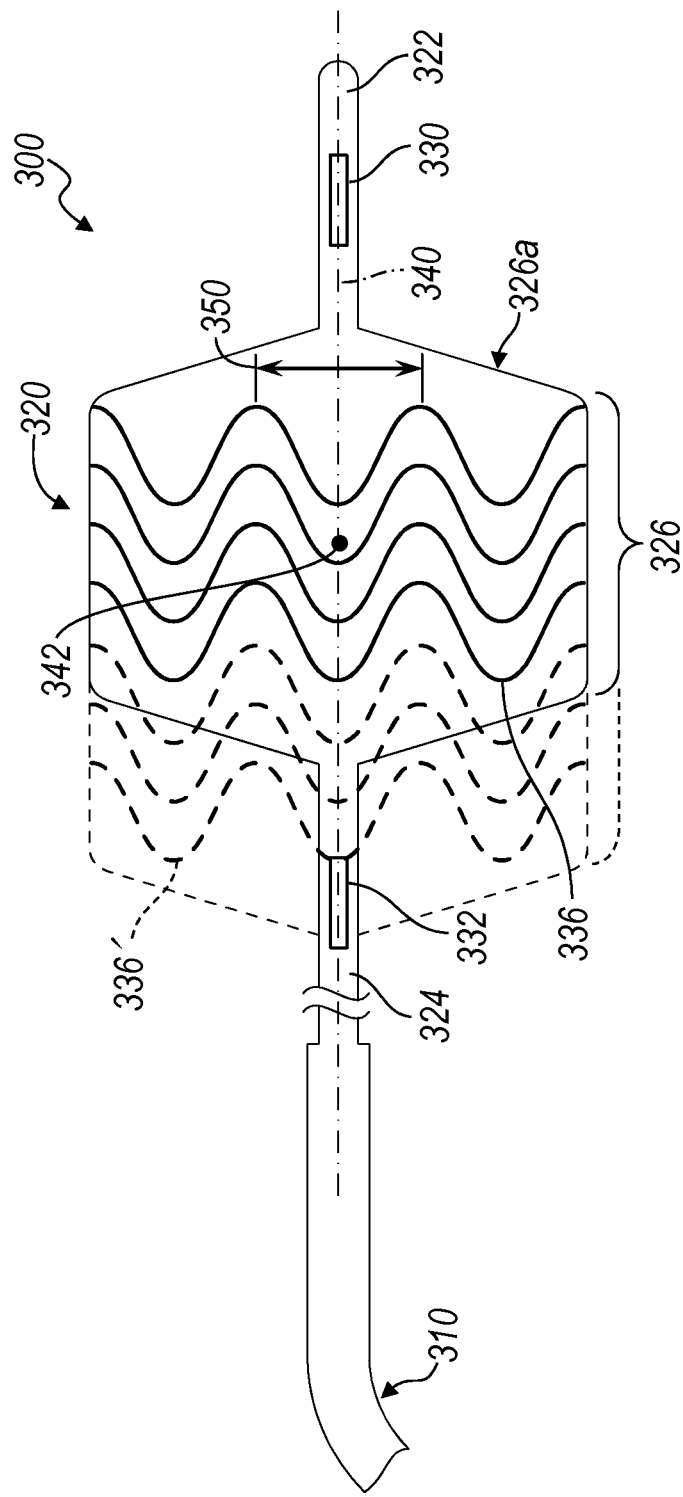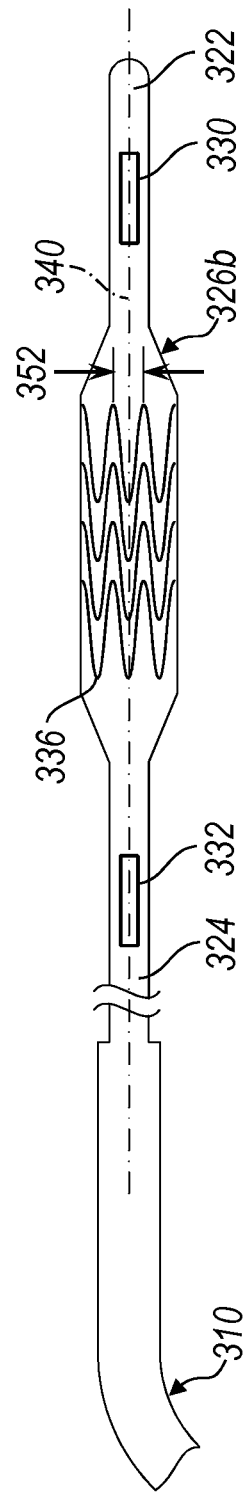
FIG. 2A
FIG. 2B

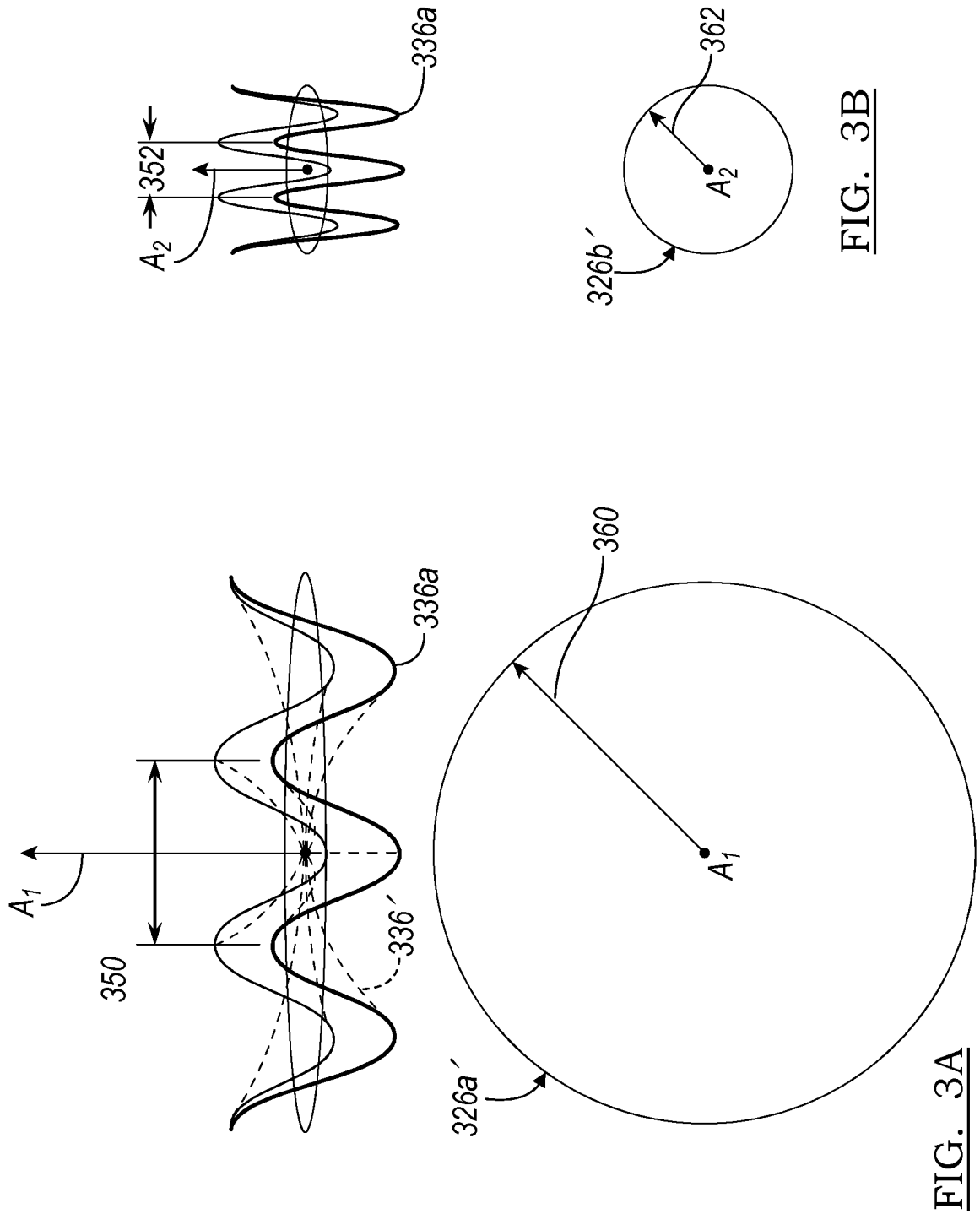

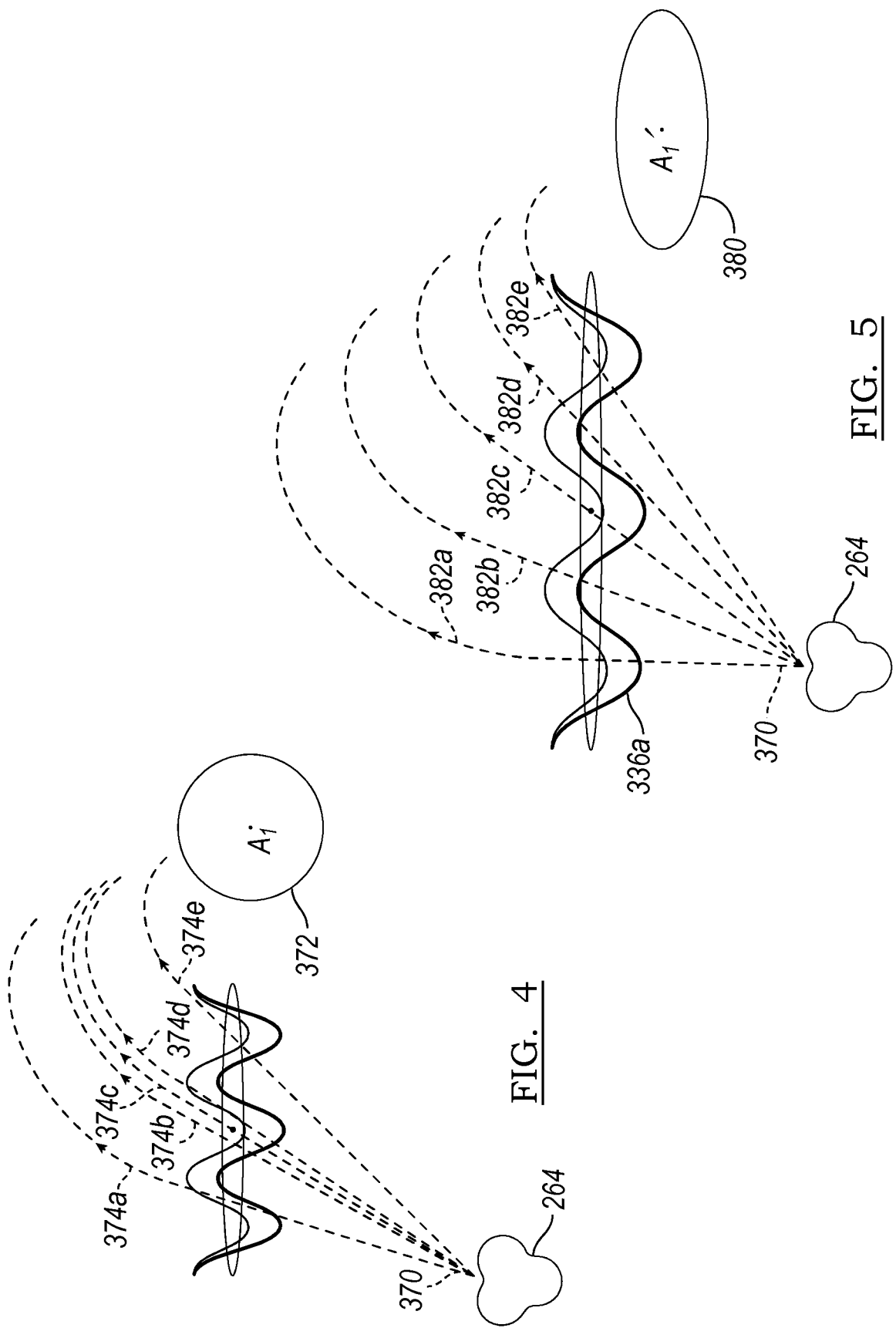

FLEXIBLE CIRCUIT COILS

FIELD

The present disclosure relates to instrumentation, and particularly relates to selected instruments having flexible portions for various procedures.

BACKGROUND

This section provides background information related to the present disclosure which is not necessarily prior art.

Instruments can be navigated within a navigation volume using various tracking systems. The tracking system can be used to determine the location of an instrument or portion associated with the instrument. For example, a tracking device can be positioned on a proximal portion of an instrument, such as the portion generally held or manipulated by a user. A distal end or working end of the instrument can be inserted into a subject, including an anatomic object or an inanimate object, for performing a procedure thereon. Procedures may include surgical procedures such as a balloon dilation or catheterization and non-surgical procedures such as repairs in hidden work spaces of mechanical or electrical devices or assembly of the same.

SUMMARY

This section provides a general summary of the disclosure, and is not a comprehensive disclosure of its full scope or all of its features.

Tracked instruments can be used for various procedures, such as repair procedures, surgical procedures, or in other instances. The instrument may include deformable portions, such as an inflatable or balloon portion. Generally, the inflatable or balloon portion is near a distal end or working end of the instrument that is spaced away from a user. The inflatable portion, therefore, may be more efficiently tracked with the tracking device positioned adjacent or near to the inflatable portion.

A tracking device may include a conductive material, such as a wire, that is positioned adjacent to or on the surface of the inflated portion. For example, a flexible conductor may be placed on the surface of a balloon in a selected pattern. The tracking device, included in the flexible conductor, can then be used to track the location of the tracking device in an electromagnetic field as is generally understood in the art, and discussed further herein. Further, as the inflatable portion (also referred to as a balloon herein) inflates and/or deflates, the flexible conductor will experience the electromagnetic field in a different manner due to the changing shape and spacing of the flexible conductor. Therefore, the flexible conductor may not only be used to determine the location of the instrument, including the balloon, but may also be used to determine a size and a configuration of the balloon as well. The position and configuration may then be displayed on a display device for viewing by a user.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is an inflated view of an instrument;

FIG. 2B is a deflated view of the instrument of FIG. 2A;

FIG. 3A is a schematic cross-sectional view of the expandable portion and a coil portion of FIG. 2A;

FIG. 3B is a schematic cross-sectional view of the expandable portion and coil portion of FIG. 2B;

FIG. 4 is a schematic cross-sectional view and flux illustration, according to various embodiments; and FIG. 5 is a schematic cross-sectional view of an instrument in flux configuration according to various embodiments.

Corresponding reference numerals indicate corresponding parts throughout the several views of the drawings.

DETAILED DESCRIPTION

Figure 1:
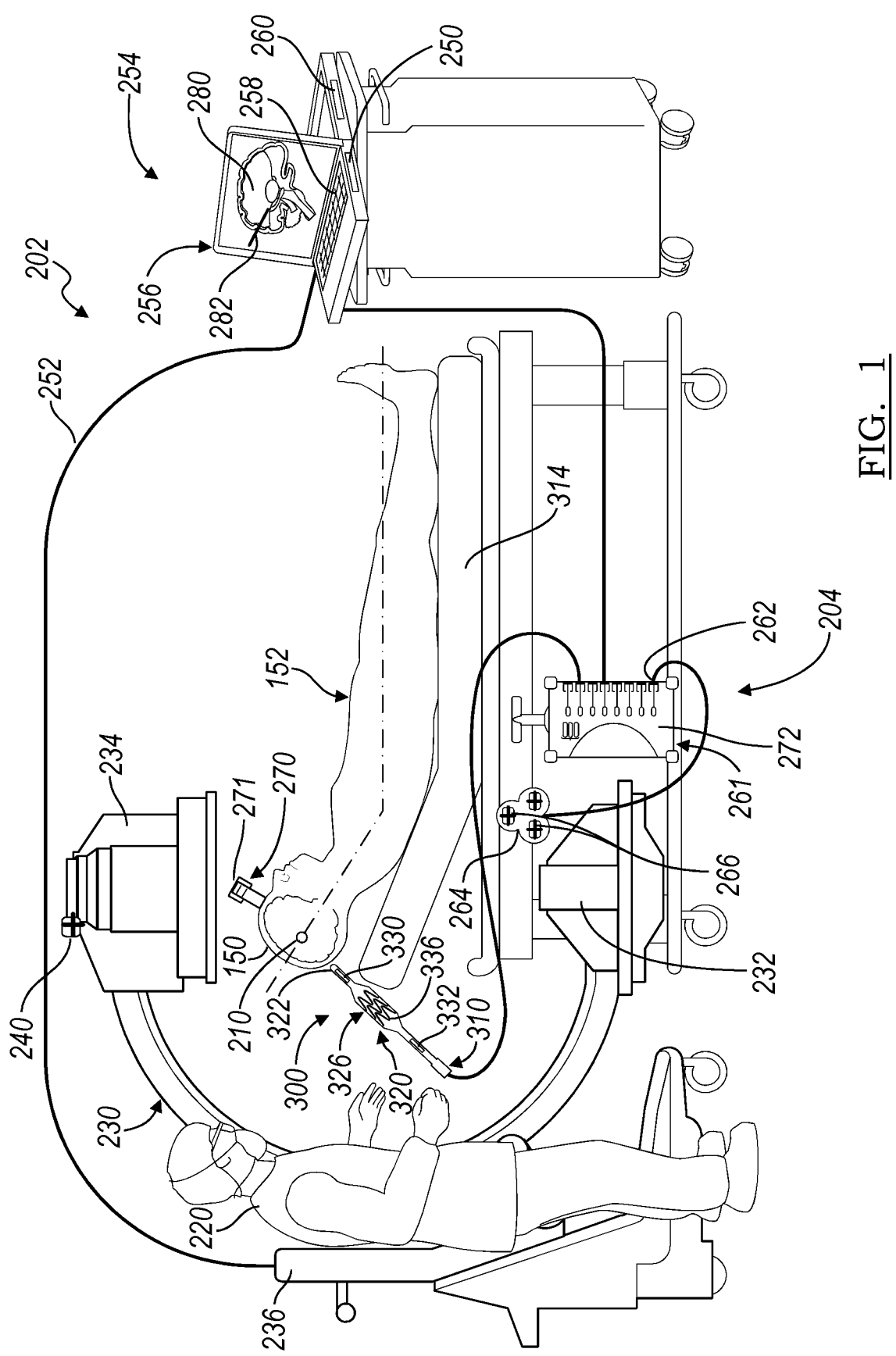
FIG. 1 is a schematic view of a navigation system.

Example embodiments will now be described more fully with reference to the accompanying drawings.

An exemplary electromagnetic (EM) navigation system 202 is shown in FIG. 1. Although the EM navigation system 202 is primarily described with respect to performing a procedure on a human patient 152, the EM navigation system 202 may be used to perform a procedure on other animate and/or inanimate subjects. Also, the implementations disclosed herein may be applied to other EM systems and for purposes other than for position tracking of devices. For example, the implementations may be used to generate EM fields in a transcranial magnetic stimulation system. Also, procedures disclosed herein can be performed relative to a volume, a mechanical device, and/or an enclosed structure. The volume may be of an animate or inanimate object. The subject can be an object that includes an enclosed mechanical device.

With reference to FIG. 1, an instrument assembly may include an appropriate tool or instrument, such as one including a handle or motor and a toolkit. The instrument 300 may include a portion that is positioned relative to, such as within, a skull 150 of the subject 152. The tool assembly 300 may include a tracking device 330, 332, 336 and may be a navigated instrument. The instrument 300 is merely exemplary, and other navigated instruments may include catheters, leads, stimulators, etc. Also, the tracking device 330, 332, 336 may be incorporated into a separate element, such as a removable stylet. The stylet may be placed within a lumen of a catheter.

The tracking device 330, 332, 336 may be interconnected with the navigation system 202. The navigation system 202, as discussed further herein, may include a tracking system 204 that can track the tracking device 330, 332, 336 in six degrees of freedom, including three-dimensional space including a X, Y, Z location and various orientations to determine a position of the tracking device 330, 332, 336 in space. As illustrated above, the instrument 300 may include the tracking device 330, 332, 336 that allows for directly tracking the tool 300 during an implantation and positioning of tool 300. Appropriate tracking devices can include tracking devices as disclosed in U.S. Pat. No. 8,644,907, incorporated herein by reference. Additionally, the navigation system can include the navigation system disclosed in U.S. Patent Application Publication 2014/0323852, incorporated herein by reference.

With continuing reference to FIG. 1, the tool 300 may be inserted into an opening or bore 210 in the skull 150 of the subject 152. The bore 210 may be a burr hole formed through the skull 150 as generally understood in the art. The tool 300 may be tracked either directly via the tracking device 330, 332, 336 or via the tracking device on a stylet or other portion associated with the tool 300. Further, as noted above, the tracking device 330, 332, 336 may be associated directly with the tool tip. Thus, any one or more of these may be used to track the selected portion of the tool assembly 300. Further, the tool 300 may be a catheter that is placed in a vasculature of the subject 152, a nasal cavity, or other portion of the subject 152.

The navigation of the tool assembly 300 relative to the subject 152 may proceed according to various navigation procedures and techniques, such as those generally known in the art and discussed below, to ensure or assist in positioning the instrument 300 in a selected, including a predetermined or preselected location, within the subject 152. Further, although the following description is related generally to positioning the tool assembly 300 relative to the skull 150 of the subject 152, other navigated procedures may be performed.

The navigation system 202, which may include an electromagnetic navigation system, is primarily described with respect to performing a procedure on a human patient, the navigation system 202 may be used to perform a procedure on other animate and/or inanimate subjects, including those navigation systems as disclosed in U.S. Pat. App. Pub. No. 2014/0323852, incorporated herein by reference. Also, procedures disclosed herein can be performed relative to a volume, a mechanical device, and/or an enclosed structure. The volume may be of an animate or inanimate object. The subject can be an object that includes an enclosed mechanical device.

The navigation system 202 assists in performing a navigated or guided procedure. The guided procedure can be, for example, a surgical procedure, a vasculature procedure, a cardiac procedure, a neural procedure, a spinal procedure, and an orthopedic procedure. The navigation system 202 allows a user, such as a surgeon 220, to view on a display 256 a position of the tool assembly 300 in a coordinate system. The coordinate system can be related to an image, such as in an image guided procedure, or can be related to an imageless procedure.

The navigation system 202 can operate as an image-based system or as an imageless system. While operating as an imageless system, the navigation system 202 can register a subject space (generally defined within and near the subject 152) to a graphical display representing an area of the subject 152, rather than to both the subject space and an image space. Image data of the subject 152 need not be acquired at any time, although image data can be acquired to confirm various locations of instruments or anatomical portions of the subject 152. Positions of the subject 152 can be tracked and positions of the tool assembly 300 relative to the subject 152 can be tracked.

While operating as an imageless system, a position of an anatomical structure can be determined relative to the instrument and the positions of the anatomical structure and the instrument can be tracked. For example, a plane of an acetabulum can be determined by touching several points with the tool assembly 300, or selected tracked tool with at least one of the tracking devices 330, 332, 336. As another example, a position of a femur can be determined in a similar manner. The position of the tool assembly 300 and the anatomical structure can be shown on a display with icons or graphics. The display, however, may not show actual image data captured of the subject 152. Other data can be provided, such as atlas data or morphed atlas data. The atlas data can be image data that is generated or generalized from the subject 152. For example, a brain atlas can be generated based on detail analysis of image data of a brain of a patient. Operation of the navigation system 202 as an image based system is further described below.

Although the navigation system 202 is described as acquiring image data using an imaging device 230, other data may be acquired and/or used, such as patient and non-patient specific data. The imaging device 230 acquires pre-, intra-, or post-operative image data and/or real-time image data of a subject 152. The imaging device 230 can be, for example, a fluoroscopic x-ray imaging device that may be configured as a C-arm having an x-ray source 232 and an x-ray receiving device 234. Other imaging devices may be included and mounted on the imaging device 230. Calibration and tracking targets and radiation sensors may be included with the imaging system 230.

The navigation system 202 may further include an imaging device controller 236. The imaging device controller 236 controls the imaging device 230 to (i) capture x-ray images received at the x-ray receiving section 234, and (ii) store the x-ray images. The imaging device controller 236 may be separate from the imaging device 230 and/or control the rotation of the imaging device 230. For example, the imaging device 28 can move in selected directions around the patient 152. Also, the imaging device may include an O-Arm® imaging device as sold by Medtronic, Inc., having a place of business in Minnesota.

Further, an imager tracking device 240 may be included to track a position of selected portions of the imaging device 230 to identify the position of the imaging device 230 relative to the subject 152 while acquiring the image data to assist in registration. The image data can then be forwarded from the imaging device controller 236 to a processing module of a navigation computer 250 wirelessly or via a link 252. The navigation computer 250 can include a processing module that is configured to execute instructions to perform a procedure.

A work station 254 can include the navigation computer 250, a navigation display 256, a user interface 258, and an accessible memory system 260. The image data may be transmitted from the controller 236 to the work station 254 or to a tracking system 204. The workstation 254 may be a portable computer, such as a laptop computer or a tablet computer. The navigation computer 250 including the computer module may include a general purpose processor that executes instructions for navigating the tool assembly 300 and/or may include an application specific circuit. The tracking system 204, as discussed further herein, may include a coil array controller (CAC) 261 having a navigation device interface (NDI) 262.

While the imaging device 230 is shown in FIG. 1, any other alternative 2D, 3D or 3D imaging acquired over time to include four dimensions, imaging modality may also be used. Examples include those discussed above, and further any imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative, computed tomography (CT), single photo emission computed tomography (SPECT), and/or planar gamma scintigraphy (PGS) imaging devices may be used. Any of these imaging devices may be used to acquire pre- or post-operative and/or real-time images or image data of the subject 152. The images may also be obtained and displayed, generally, in two or three dimensions. In more advanced forms, 3D surface rendering regions are achieved of the subject, which may be rendered or changed in time (fourth dimension). The 3D surface rendering regions may be achieved by incorporating subject data or other data from an atlas or anatomical model map or from pre-operative image data captured by MRI, CT, or echocardiography modalities. Image data sets from hybrid modalities, such as positron emission tomography (PET) combined with CT, or single photon emission computer tomography (SPECT) combined with CT, can also provide functional image data superimposed onto anatomical data to be used to reach target sites within the subject 152.

The navigation system 202 further includes the tracking system 204. The tracking system 204 includes a localizer 264, which may also be referred to as a transmit coil array (TCA), a tracking array, or a transmit coil assembly. The TCA 264 includes one or more coil groups or sets 266, as discussed further herein, that can transmit or receive a signal and/or generate a field. The tracking system 204 may include the CAC 261, the localizer 264, and the instrument tracking device 330, 332, 336 of the tool assembly 300. It is understood that the tracked portion may be generally referred to as an instrument and that the tracking device may be generally referred to as an instrument tracking device. The tracking system may also track a dynamic reference frame (DRF) 270. All tracked portions are connected to the CAC 261 via the NDI 262. The CAC 261 and the NDI 262 can be provided in a CAC/NDI container 272. The NDI 262 may have communication ports that communicate with the localizer 264, the instrument tracking device 330, 332, 336 and/or the DRF 270 wirelessly or via wires.

The coil arrays localizer 264 can transmit signals that are received by the DRF 270 and at least one tracking device 271 (e.g., the instrument tracking device 330, 332, 336). The tracking device 330, 332, 336 can be associated with the tool assembly 300 at a location that is generally positioned within the subject 152 during a procedure. The DRF 270 can then transmit and/or provide signals, from the DRF tracking device 271, based upon the received/sensed signals of the generated fields from the localizer 264 and/or other localizers. It is understood that the tracking system may also be operated in reverse, where the tracking devices 330, 332, 336, 271 transmit a field that is sensed by the TCA 264.

The DRF 270 can be connected to the NDI 262 to forward the information to the CAC 261 and/or the navigation computer 250. The DRF 270 may be fixed to the subject 152 and adjacent to the region where navigation is occurring such that any movement of the subject 152 is detected as relative motion between the localizer 264 and the DRF 270. The DRF 270 can be interconnected with the subject 152. Any relative motion is indicated to the CAC 261, which updates registration correlation and maintains accurate navigation.

In operation, the navigation system 202 creates a map between points in image data or an image space, such as one defined by an image 280 shown on the display 256, and corresponding points in a subject space (e.g., points in an anatomy of a patient or in a patient space). After the map is created, the image space and subject space are registered to each other. This includes correlating position (location and orientations) in an image space with corresponding positions in a subject space (or real space). Based on the registration, the navigation system 202 may illustrate an icon 282 (which may include a three-dimensional rendering of the instrument, including the tool assembly 300) at a navigated position of the tool assembly 300 relative to an image of the subject 152 in a super-imposed image. For example, the icon 282 can be illustrated relative to a proposed trajectory and/or a determined anatomical target. The work station 254 alone and/or in combination with the CAC 261 and/or the C-arm controller (or control module) 236 can identify the corresponding point on the pre-acquired image or atlas model relative to the tracked tool assembly 300; and display the position on display 256 and relative to the image 280. This identification is known as navigation or localization. The work station 254, the CAC 261, and the C-arm controller 236 and/or selected portions thereof can be incorporated into a single system or implemented as a single processor or control module.

To register the subject 152 to the image 280, the user 220 may use point registration by selecting and storing particular points from the pre-acquired images and then touching the corresponding points on the subject 152 with a pointer probe or any appropriate tracked device. The navigation system 202 analyzes the relationship between the two sets of points that are selected and computes a match, which allows for a correlation of every point in the image data or image space with its corresponding point on the subject 152 or the subject space.

The points that are selected to perform registration or form a map are the fiducial markers, such as anatomical or artificial landmarks. Again, the fiducial markers are identifiable on the images and identifiable and accessible on the subject 152. The fiducial markers can be artificial landmarks that are positioned on the subject 152 or anatomical landmarks that can be easily identified in the image data.

The navigation system 202 may also perform registration using anatomic surface information or path information (referred to as auto-registration). The navigation system 202 may also perform 2D to 3D registration by utilizing the acquired 2D images to register 3D volume images by use of contour algorithms, point algorithms or density comparison algorithms.

In order to maintain registration accuracy, the navigation system 202 tracks the position of the subject 152 during registration and navigation with the DRF 270. This is because the subject 152, DRF 270, and localizer 264 may all move during the procedure. Alternatively the subject 152 may be held immobile once the registration has occurred, such as with a head holder. Therefore, if the navigation system 202 does not track the position of the subject 152 or an area of an anatomy of the subject 152, any subject movement after registration would result in inaccurate navigation within the corresponding image. The DRF 270 allows the tracking system 204 to track the anatomy and can be used during registration. Because the DRF 270 is rigidly fixed to the subject 152, any movement of the anatomy or the localizer 264 is detected as the relative motion between the localizer 264 and the DRF 270. This relative motion is communicated to the CAC 261 and/or the processor 250, via the NDI 262, which updates the registration correlation to thereby maintain accurate navigation.

The tracking system 204 can position the localizer 264 adjacent to the patient space to generate an EM field (referred to as a navigation field). Because points in the navigation field or patient space is associated with a unique field strength and direction, the tracking system 204 can determine the position (which can include location and orientation) of the tool assembly 300 by measuring the field strength and direction or components of the EM field at the tracking device 330, 332, 336. The DRF 270 is fixed to the subject 152 to identify the location of the subject 152 in the navigation field. The tracking system 204 continuously determines the relative position of the DRF 270 and the tool assembly 300 during localization and relates this spatial information to subject registration data. This enables image guidance of the tool assembly 300 within and/or relative to the subject 152.

To obtain a maximum accuracy it can be selected to fix the DRF 270 in each of at least six degrees of freedom. Thus, the DRF 270 or any tracking device, such as the tracking device 330, 332, 336, can be fixed relative to axial motion X, translational motion Y, rotational motion Z, yaw, pitch, and roll relative to a portion of the subject 152 to which the DRF 270 is attached. Any appropriate coordinate system can be used to describe the various degrees of freedom. Fixing the DRF 270 relative to the subject 152 in this manner can assist in maintaining maximum accuracy of the navigation system 202.

The tool assembly 300 can include the stylet, drill, etc., as discussed above. Thus, reference to the tool assembly 300 is not intended to limit the instrument that may be tracked and navigated. With reference to any appropriate navigated instrument, it may include the tracking device 330, 332, 336 that may include a power source or may be powered from an external source. The power supply may be charged, as discussed above, and the tool may be tracked with the navigation system as discussed above.

The instrument 300, as illustrated in FIGS. 1, 2A, and 2B, may include a handle or manipulating portion 310 in addition to a working portion 320 extending from the handle portion 310. The working portion 320 may include a distal terminal tip 322 and a proximal portion 324 that generally may extend to or contact a balloon or inflatable portion 326. The tool may, according to various embodiments, be a catheter, such as a balloon catheter, including the NC Euphora™ Noncompliant Balloon Dilatation Catheter or the Sprinter® OTW Semi-compliant Over-the-Wire Balloon Dilatation Catheter, NuVent™ sinus dilation system, all sold by Medtronic, Inc.

The distal tip 322 and the proximal tip or portion 324 can contact or be immediately adjacent to the inflatable portion 326. Therefore, the working end 320 may include the inflatable portion 326 and other portions associated therewith. In particular, the distal tip 322 may be used for manipulating various tissues, and/or for cannulating various orifices such as a coronary sinus ostium (CSOS). The inflatable portion 326 may be provided for various procedures, such as those generally understood in the art that may be assisted by inflating the inflatable portion 326, such as to increase internal diameters of a vessel.

The various portions of the working end 322 may also include tracking members, such as a first or distal tracking member 330, a proximal tracking member 332, and a flexible conductor tracking portion 336. Each of the tracking portions 330, 332, and 336 can be tracked with the tracking system 204 to allow for tracking and navigating the working portion 320 of the instrument 300. Each of the tracking portions 330-336 may include windings or tracking coils, such as a winding portion 336a.

As discussed above, the tracked location of the working end 320, including the various portions thereof, can be illustrated on the display device 256 for various procedures. The procedure may include a neuro-procedure, vasculature procedure, stent placement procedure, sinus dilation, sinus opening dilation, or other appropriate procedures. Additionally, non-surgical interventions may occur such as placing the working end 320 in an inanimate object, such as in a flow system of a refrigeration system, lubricating system for a mechanical operating device, or the like. Accordingly, the presently disclosed system is not limited to a surgical intervention system, although specific examples included herein relate thereto.

The tracking devices 330, 332 may differ from the flexible tracking device 336, or may be substantially similar. In various embodiments, the distal tracking device 330 and the proximal tracking device 332 may be micro-coils, such as the micro-coils included in the Malleable Suction™ ENT suction instruments sold by Medtronic, Inc.; the Malleable Suction™ instruments may include integrated coils that are trackable with the AxiEM® surgical navigation system sold by Medtronic, Inc. The micro-coils may be those that are designed and/or manufactured for use in the Malleable Suction™ instruments. The micro-coils 330, 332 can be introduced into the instrument at the proximal portion 324 and the distal portion 322 such as by laminating therein, adhering to an exterior, or otherwise attached to the instrument 300. The micro-coils 330, 332 may generally be substantially rigid such that they will not flex or bend easily. Generally, the rigidity of the micro-coils 330, 332 is such that they can be introduced into a selected subject, such as into a heart, vasculature, neurosystem, or the like of a human subject, without being deformed by contact with tissue of the subject 152. The micro-coils 330, 332 can either sense a field, such as an EM field, emitted by the localizer 264 or emit a field that is sensed by the localizer 264 to allow for a determination of a tracked location of the instrument 300 including the working end 320 of the instrument 300. The determination of a location of the micro-coils 330, 332 can be used to assist in determining a location of the working end 320 of the instrument 300. Generally, the determination of a location of the instrument 300 can be similar to the tracking of an instrument as discussed above.

The flexible tracking coil or portion 336, however, may be formed with the flexible portion or balloon 326 such that its configuration, including shape and size, may change due to inflation or deflation of the balloon portion 326. It is understood that the inflatable portion 326 may, however, change in other configurations different than only inflating to increase a diameter uniformly. Generally, the inflatable portion may be understood to be a portion that is able to change from one configuration to another, such as folded or compact to another configuration, such as unfolded. Further, the change may be reversible, such as deflation.

In addition, it is understood that the inflatable portion 326 need not be a single portion and that more than one flexible coil 336 may be associated therewith. For example, the inflatable portion 326 may be larger and include two or more of the flexible coils that are spaced apart. As illustrated in FIG. 2A one coil 336 may be near the distal tip and a second coil 336' (shown in phantom) may be nearer the proximal portion. Further, each of the flexible coils 336, 336' may be able to change configuration independently of the other flexible coil 336, 336'. Any appropriate number of the coils 336 may be provided, however, on the expandable portion 326.

With continued reference to FIG. 2A and additional reference to FIG. 2B, the balloon portion 326 may include an inflated configuration 326a as illustrated in FIG. 2A, and a deflated configuration as illustrated at 326b in FIG. 2B. The flexible tracking coil 336, however, may be maintained on the flexible portion 326 in either configuration, although the configuration of the flexible coil 336 may change. The flexible coil 336 may be a coil of wire formed around the flexible portion 326 in several wraps, according to generally known coiling techniques. Thus, the flexible coil 336 may be formed of one or more coil wraps that are wound around the balloon portion 326. All of the windings may act as a single coil according to generally know tracking portions.

The flexible coil 336 can be formed separately and applied to the flexible portion 326, such as being formed on a flexible circuit and adhered or integrated, such as with a lamination, into the flexible portion 326. Alternatively, the flexible wire 336 may be selectively adhered to the exterior or to a layer of the flexible portion 336 such as with a flexible adhesive. Also, or alternatively, the flexible portion 336 may have a wire that is connected with a slip mechanical connection, such as a thread or grommet that allows the wire of the flexible circuit 336 to move when expanding or contracting without breaking the strand or wire forming the flexible coil 336. Further, the flexible coil 336 may be integrated, such as on a layer of lamination, of the flexible member 326.

Regardless of the assembly construction of the flexible coil 336, the flexible coil 336 may operate as a tracking device similar to the tracking devices 330, 332 to assist in determining a location of the flexible portion 326. Generally, the flexible coil 336 is formed around an axis 340 of the flexible portion 326 and further may be formed around a center point 342 of the flexible portion 326. Thus, the flexible coil 336 can be used to determine a location and orientation of the flexible portion 326 in a manner similar to the coils 330, 332 for individually determining locations of other specific portions of the instrument 300.

The flexible coil 336 may be used to determine a location of the flexible portion 326, in a manner similar to that discussed above, a field emitted by the localizer 264 may be sensed by the flexible coil 336. The winds, such as the portion 336a, of the flexible coil 336, however, may change configuration based upon the amount of inflation or deflation of the flexible portion 326, as illustrated in FIGS. 2A and 2B.

As illustrated in FIGS. 2A and 2B, the flexible coil 336 may be wound around the flexible portion 326 in a wave, such as sinusoidal wave, pattern. Therefore, as illustrated in FIG. 2A, in the inflated configuration 326a, a first distance 350 may be formed between adjacent peaks of the wave winding formation of the flexible coil 336. As illustrated in FIG. 2B, a second distance 352 may be formed between the same two adjacent peaks of the wound wave formation of the flexible coil 336. Accordingly, the field sensed by the flexible coil 336 may differ between the inflated configuration 326a of the balloon 326 and the deflated 326b configuration of the balloon 326. The difference of the flexible coil 336 may, at least in part, be based upon at least the distance 350 as compared to the distance 352 between the adjacent peaks of the flexible coil 336.

The flux of the field sensed by the flexible coil 336 may also differ based upon the orientation and/or size of the air core of the wire of the flexible coil 336 in the field, as discussed further herein. Although the field sensed by the flexible coil 336 may differ between the inflated configuration 326a and the deflated configuration 326b, the location of the center point 342 of the flexible portion 326 need not change. Accordingly, the flexible coil 336 may be used to determine the location of the working portion 320 either alone or in combination with the tracking coils 330, 332.

The expandable portion 326 may be configured in any appropriate geometry, such as including a substantially cylindrical configuration including a straight outer wall that may terminate in angled or tapered walls towards the central axis 340. Alternatively, the expandable portion 326 may be substantially spherical in configuration having a center and a substantially equal radius extending from the center to all of the edges of the expandable portion 326. Regardless of the configuration of the expandable portion 326, however, the flexible coil 336 may be provided and used to determine a geometry of the expandable portion, or a portion of the expandable portion 326 (e.g., that portion of the expandable portion 326 including the flexible coil 336 provided thereon) according to various embodiments as illustrated herein.

With additional reference to FIGS. 3A and 3B, a schematic cross-sectional view of the expandable portion 326 is illustrated as 326a'. The expanded expandable portion 326a' may include a radius of 360. A single winding 336a of the flexible coil 336 having the distance 350 between peaks may have an area through which a magnetic field may have flux. The expanded coil area formed by coil 336a may enclose a large magnetic field flux due to the expanded portion of the coil 336a on the inflated expandable member configuration 326a. A large effective area and direction is illustrated by vector $A_1$ illustrated in FIG. 3A. Though it is understood that magnetic flux is a scalar value, its effect on the coil may be in a direction due to a configuration of the coil within the field. Generally, in the expanded configuration, the area within the coil winding 336a can extend from the physical coil winding 336a towards a center of the coil winding, which may be along the axis 340, according to various embodiments. Generally, the vector $A_1$ can be aligned with the axis 340. However, as illustrated in FIG. 3A, the area of the coil may define a "surface" (as illustrated by surface lines 336' extending from the coil portion 336a towards the vector line $A_1$). As the magnetic field passes through the surface 336' each area (generally understood to be an infinitesimal small area of the surface) will experience a portion of the entire flux of the magnetic field. At the surface, the infinitesimal area vector will be in a generally unique direction based upon the curvature of the coil member 336a as illustrated in FIG. 3A. Each of the infinitesimal vectors dAi dot into the magnetic field vectors passing through that area and, therefore, relate to the amount of flux through the surface area of the coil 336a to account for the full flux $A_1$, as illustrated in FIG. 3A.

With reference to FIG. 3B, a cross-section expandable member area 326b' may include a radius 362 that is smaller than the radius 360. Accordingly, the coil portion 336a may include the distance 352 between adjacent coil peaks in the unexpanded configuration. As the radius 362 is smaller than the radius 360, the distance 352 between respective peaks is smaller than the distance 350 and the area formed or defined by the coil portion 336a is smaller. As the area is smaller, the effective area and representation is a smaller vector $A_2$, illustrated in FIG. 3B. In other words, if the center points and directions of the respective coil members in the different sizes (e.g. 350, 352) defined by vectors A1 and A2 align (i.e. are aligned in space in the same field), then the larger area A1 will, in general, intersect more magnetic field vectors than the smaller area A2. As such, the expanded coil member 336a having the distance 350 and the vector A1 will measure larger flux and electrical signal than the smaller coil member 336a having the distance 352 and the vector A2.

The amount of flux through the coil portion 336a can be determined with the tracking system 204 according to generally known techniques for measuring electromagnetic signals, such as based upon an induced current in the coil portion 336 or the entire coil 336. The greater the flux through the coil the greater the gain, such as including the greater the signal through the flexible coil 336, the greater the expansion of the expandable member 326 based upon the measured increased gain due to the increased flux through the coil surface area. Such a determination can be used to determine the amount of expansion of the flexible member 326 and can be used to determine a shape or configuration of the expandable portion.

With reference to FIG. 4, and continued referenced to FIG. 3A, a field flux that emanates from the localizer 264 may be along field lines 370 that extend from the localizer 264 as generated by the TCAs included therein. Numerous field lines pass through the area defined by the coil portion 336a at various angles relative to the "surface" defined by the coil 336a. Illustrated in FIG. 4 are exemplary angles that the field lines 370 may extend through the "surface" due to the configuration of the coil portion 336a in a selected configuration of the expandable portion 326, for example, when it is formed as a circle 372. The exemplary angles or vectors are defined by the field lines that pass through the coil surface at vectors 374a-374e. Each of the vectors will affect the coil and generate a signal in the coil portion 336a of the coil 336 based upon the amount of flux through the coil 336 due to the configuration of the expandable portion 326, for example when it is generally circular 372. The signal generated based upon the configuration may differ from a signal through the coil portion 336a of the coil 336 when the expandable portion 326 is generally in an oval configuration 380 as illustrated in FIG. 5.

As illustrated in FIG. 5, the field lines 370 extending from the localizer 364 may intersect the "surface" defined by the coil portion 336a in a manner different than the angles 374a-374e when the expandable portion is in a circle cross-section. For example, as illustrated in FIG. 5, the field lines 370 may intersect the "surface" at vector angles or along vectors 382a-382e. The signal generated from the coil 336 due to the sum of field along the vectors 382a-382e is different due to the configuration of the expandable portion 326 having the oval cross-section 380.

The two different signals can be used to determine the configuration (e.g. geometry, size, volume, shape, etc.) of the expandable portion 326 as the expandable portion expands from the collapsed configuration 326b to the expanded configuration 326a, and vice versa. It is understood, however, that more than two signals may be received from the coil 336 due to multiple, independent magnetic fields generated from the coils of the coil sets 266 within TCA 264 and due to more than two possible configurations. For example, the expandable portion 326 may go through an infinite number of configuration changes form the collapsed configuration 326b to the expanded configuration 326a. Accordingly, the navigation system 202 can be used to determine the geometry of the expandable portion 326 based upon the signal from the coil 336. As discussed herein, the determined configuration may be displayed and the user may view the determined configuration. Thus, the size of the expandable portion 326 can be determined based upon the amount gained through the coil 336 and/or the configuration of the expandable portion 326 can be determined based upon the signal through the coil 336.

According to various embodiments, the position, size, orientation, and/or configuration of the expandable portion 326 can be determined by various algorithms. Without being bound by the theory, the signal received by the navigation system 202 from the coil 336 is due to the position, orientation, and configuration, including both the shape and size of the coil 336, having the EM field flux through the coil 336 in the navigable volume.

A plurality of configurations, such as different shapes and amounts of expansion, between the collapsed configuration 326b and the expanded configuration 326a of the expandable portion 326 can be determined by a matching algorithm. The different position, orientation and configurations of the expandable member 326 can be stored in a look-up table in the memory system 260. A signal from the coil 336 can be predetermined, as well, due to each of the plurality of position, orientation and configurations of the expandable portion 326. The signal can be measured in a calibration analysis and/or modeled. During use in a procedure, then, the signal received by the navigation system 202, such as through the CAC 261, can be compared to the look-up table stored in the memory system 260 to determine the position, orientation and configurations and size of the expandable portion 326 during the procedure. The determination may be made in real time or at a determined time interval.

It is understood, however that a parameter may also be defined for the shape or size. For example, an elliptical shape along with a shape parameter such as an elliptical eccentricity. Further parameters may include orientation in the field. One or more of the parameters either alone or with position, orientation and configurations may be saved in the table to assist in determining the current position.

If the signal does not identically match a signal in the look-up table, an iterative process can be used to determine the position, orientation and configurations, including shape and size, of the expandable portion 326 through interpolation between at least two stored signals and/or configurations. The iterative process may be according to generally known iterative or matching processes, including various optimization algorithms such as gradient descents. The process may begin with determining two nearest signals, such as one greater and one lesser than the received signal. In this manner, the navigation system 202 can be used to determine the current position, orientation and configurations (e.g. in use configuration), including the size and the shape, of the expandable portion 326 within the subject 152.

To determine the current configuration of the coil 366, however, starting with a matching is not required. For example, an appropriate starting point for an algorithm may include a last know configuration, a random starting point regarding position and configuration, a subsets of points based on a summing, or other appropriate starting point. Further, the determination may use one or an appropriate number of stored shapes, sizes, configurations, or parameters.

In light of this, all of the location, size, and shape of the expandable portion 326 can be displayed on the display device 256. Additionally, the location, size, and shape can be displayed as the icon 282 superimposed on the image 280 of the subject 152. In light of the determined size and shape, a rendering, such as a three-dimensional rendering, can also be displayed as the icon 282.

The working portion 320 of the instrument 300 may, therefore, be displayed on the display device 256 for viewing the by the user 220. Although the user 220 may not be able to directly visualize the working portion 320 within the subject 152, the signal received by the navigation system 202 can be used to determine the location, size, and configuration of the expandable portion 326 within the subject 152.

In addition, it is understood that various tracking devices can be positioned on the expandable portion 326. For example, fixed or generally rigid coil portions can be provided in or integrated into the expandable portion 326 rather than providing the flexible coil 336. The rigid coils, however, may run into the amount of expansion and shape change of the expandable member 326 in various embodiments.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for determining a configuration of an expandable portion, comprising:
   an instrument having a first end and a second end and an expandable portion between the first end and the second end, wherein the expandable portion is configured to change from a first configuration to a second configuration;
   a sensing member positioned with the expandable portion of the instrument and configured to change configuration with the expandable portion from the first configuration to the second configuration;
   wherein the sensing member is configured to sense a field generated with a localizer and generate a first signal based on the sensed field when the expandable portion is in the first configuration and generate a second signal based on the sensed field when the expandable portion is in the second configuration; and
   a tracking processor configured to, both:
   (i) receive a signal from the sensing member, and
   (ii) execute instructions to track and determine both (a) a location of the instrument based on the signal from the sensing member and (b) at least one of a size or a shape of the sensing member based on the first signal or the second signal from the sensing member;
   wherein the sensing member includes a flexible coil having a plurality of wraps, each wrap having a transverse wave pattern wound around a longitudinal axis of the expandable portion and is able to vary configuration with the expandable portion, the transverse wave pattern having a plurality of adjacent transverse peaks extending transversely to the longitudinal axis around a perimeter of the expandable portion, where a transverse distance that is transverse to the longitudinal axis and between a pair of adjacent transverse peaks varies from the first configuration to the second configuration to vary the signal from the sensing member.

2. The system of claim 1, further comprising:
   the localizer configured to generate the field;
   wherein the field is an electromagnetic field and a flux of the electromagnetic field is sensed by the sensing member to generate the signal;
   wherein the first signal and the second signal are based on the sensed flux that differs between the first configuration and the second configuration.

3. The system of claim 1, wherein the expandable portion is a balloon having a wall;
   wherein the sensing member is an expandable coil formed in the wall.

4. The system of claim 1, further comprising:
   a tracking member configured to sense the field and generate a tracking signal based on the sensed field configured to allow a determination of a location of the expandable portion.

5. The system of claim 1, further comprising:
   a memory configured to store a look up table of at least one configuration, including size and shape, of the expandable portion;
   wherein the tracking processor is configured to execute instructions to determine at least the size or the shape of the sensing member based on the sensed field to compare the signal from the sensing member to a stored signal in the look up table to determine at least one of the size or the shape of the expandable portion.

6. The system of claim 5, wherein the tracking processor is further configured to execute instructions to interpolate from at least one stored signal to determine at least one of the size or the shape of the expandable portion.

7. The system of claim 2, wherein the sensing member includes the flexible coil of a conductive material formed with the expandable portion;
   wherein the flexible coil of conductive material is formed around the perimeter of the expandable portion;
   wherein although the sensed flux differs between the first configuration and the second configuration a location of a center point of the sensing member does not change allowing the sensing member to be used to determine the location of the expandable portion.

8. The system of claim 1, further comprising:
   a first tracking member at the first end of the instrument;
   a second tracking member at the second end of the instrument;
   wherein the expandable portion is between the first tracking member and the second tracking member.

9. The system of claim 1, wherein the flexible shape changing coil includes a first flexible shape changing coil and a second separate flexible shape changing coil that moves independent of the first flexible shape changing coil.

10. A system for determining a configuration of an expandable portion, comprising:
    an instrument having a handle portion and a working portion, the working portion extending from a proximal portion to a distal tip portion;
    an inflatable portion extending along a longitudinal axis between the proximal portion and the distal tip portion of the working portion; and
    a sensing member positioned around the longitudinal axis and a perimeter of the inflatable portion and configured to change shape with the inflatable portion, the sensing member formed as a flexible coil wound around the longitudinal axis of the inflatable portion in a transverse wave configuration, the transverse wave configuration having a wave extending transverse to and around the longitudinal axis and having a plurality of adjacent transverse peaks extending transversely to the longitudinal axis around the perimeter of the inflatable portion, where a transverse distance that is transverse to the longitudinal axis and between a pair of adjacent peaks varies from a first configuration to a second configuration;

wherein the inflatable portion is configured to change the sensing member from the first configuration to the second configuration;

wherein the sensing member is configured to sense a field to generate and deliver a first signal based on the sensed field at the first configuration and generate and deliver a second signal based on the sensed field at the second configuration;

wherein the delivered first signal is different from the second signal and changes from the first configuration to the second configuration;

wherein the delivered first signal or second signal is used to determine the configuration of the inflatable portion.

11. The system of claim 10, further comprising a first tracking member positioned at the proximal portion and a second tracking member positioned at the distal tip portion, wherein the first and second tracking members are configured to track a location of the proximal portion and the distal tip portion, respectively.

12. The system of claim 10, further comprising:
a tracking processor configured to both: (i) receive the first signal or second signal from the sensing member and (ii) execute instructions to track and determine both a location of the instrument based on the first signal or second signal generated by the sensing member and at least one of a size or shape of the sensing member based on the first signal or second signal generated by the sensing member.

13. The system of claim 10, wherein the flexible coil is a first flexible coil wound around the longitudinal axis of the inflatable portion in a first transverse wave configuration and a separate second flexible coil wound around the longitudinal axis of the inflatable portion in a second transverse wave configuration, wherein the first flexible coil can change configuration independently of the second flexible coil.

14. The system of claim 1, further comprising:
a first tracking member positioned proximal the expandable portion; and a second tracking member positioned distal the expandable portion;

wherein the first and second tracking members are configured to track a location of a proximal portion and a distal tip portion, respectively.

15. The system of claim 14, wherein the expandable portion is inflatable to change from the first configuration to the second configuration.

16. The system of claim 9, wherein the first flexible shape changing coil is wound around a longitudinal axis of the expandable portion in a sinusoidal wave pattern and the second separate flexible shape changing coil is wound around the longitudinal axis of the expandable portion in a sinusoidal wave pattern, wherein the first flexible shape changing coil and the second separate flexible shape changing coil are configured to be able to change configuration independently.

* * * * *

UNITED STATES PATENT AND TRADEMARK OFFICE
CERTIFICATE OF CORRECTION

| | | |
|---|---|---|
| PATENT NO. | : 11,478,304 B2 | |
| APPLICATION NO. | : 14/674766 | |
| DATED | : October 25, 2022 | |
| INVENTOR(S) | : Brad Jacobsen et al. | |

It is certified that error appears in the above-identified patent and that said Letters Patent is hereby corrected as shown below:

In the Specification

Column 4, Detailed Description, Line 23, Delete "28" and insert --230-- therefor Column 7, Detailed Description, Line 49, Delete "322" and insert --320-- therefor Column 10, Detailed Description, Line 51, Delete "A1 and A2" and insert --$A_1$ and $A_2$-- therefor Column 10, Detailed Description, Line 53, Delete "A1" and insert --$A_1$-- therefor Column 10, Detailed Description, Line 54, Delete "A2." and insert --$A_2$.-- therefor Column 10, Detailed Description, Line 55, Delete "A1" and insert --$A_1$-- therefor Column 10, Detailed Description, Line 57, Delete "A2." and insert --$A_2$.-- therefor Column 11, Detailed Description, Line 26, Delete "364" and insert --264-- therefor Column 12, Detailed Description, Line 36, Delete "366," and insert --336,-- therefor Signed and Sealed this
Third Day of October, 2023

*Katherine Kelly Vidal*

Katherine Kelly Vidal
*Director of the United States Patent and Trademark Office*